US007474754B2

(12) United States Patent
Aarts et al.

(10) Patent No.: US 7,474,754 B2
(45) Date of Patent: Jan. 6, 2009

(54) METHOD FOR CANCELING UNWANTED LOUDSPEAKER SIGNALS

(75) Inventors: Ronaldus Maria Aarts, Eindhoven (NL); Daniel Willem Elisabeth Schobben, Eindhoven (NL)

(73) Assignee: Koninklijke Philips Electronics N. V., Eindhoven (NL)

( * ) Notice: Subject to any disclaimer, the term of this patent is extended or adjusted under 35 U.S.C. 154(b) by 971 days.

(21) Appl. No.: 10/261,892

(22) Filed: Sep. 30, 2002

(65) Prior Publication Data

US 2003/0068048 A1 Apr. 10, 2003

(30) Foreign Application Priority Data

Oct. 3, 2001 (EP) ................................ 01203737

(51) Int. Cl.
*A61F 11/06* (2006.01)
*G10K 11/16* (2006.01)
*H03B 29/00* (2006.01)

(52) U.S. Cl. .................. 381/71.6; 381/71.8; 381/71.12; 381/74

(58) Field of Classification Search ................ 381/71.6, 381/74, 71.11, 310, 72, 309, 71.1, 71.14, 381/71.9, 71.8, 71.12
See application file for complete search history.

(56) References Cited

U.S. PATENT DOCUMENTS 4,817,149 A * 3/1989 Myers ........................... 381/1
5,737,433 A * 4/1998 Gardner ..................... 381/94.7
5,841,879 A * 11/1998 Scofield et al. ............. 381/309
5,852,667 A * 12/1998 Pan et al. ................... 381/71.1
5,937,070 A 8/1999 Todter et al. ............... 381/71.6
6,078,672 A 6/2000 Saunders et al. ........... 381/71.6
6,144,747 A * 11/2000 Scofield et al. ............. 381/309
6,741,707 B2 * 5/2004 Ray et al. ................ 381/71.11
7,110,951 B1 * 9/2006 Lemelson et al. ........... 704/270
2001/0046304 A1 * 11/2001 Rast ............................ 381/74
2002/0141599 A1 * 10/2002 Trajkovic et al. ........... 381/71.6

FOREIGN PATENT DOCUMENTS

EP 0559962 A2 9/1993
WO 9430029 A1 12/1994

* cited by examiner

*Primary Examiner*—Vivian Chin
*Assistant Examiner*—Jason Kurr

(57) ABSTRACT

In a method for canceling unwanted signals from at least one external sound source, such as a loudspeaker, by means of headphones provided with microphones, at least known sound signals from the at least one external sound source are compensated by anti-phase sound signals. These sound signals simulate the at least known sound signals from said at least one external sound source in anti-phase. Said anti-phase sound signals are generated in the headphones in response to signals derived from audio input signals of the at least one external sound source in a filter device which is controlled by the resulting microphone signals.

12 Claims, 1 Drawing Sheet

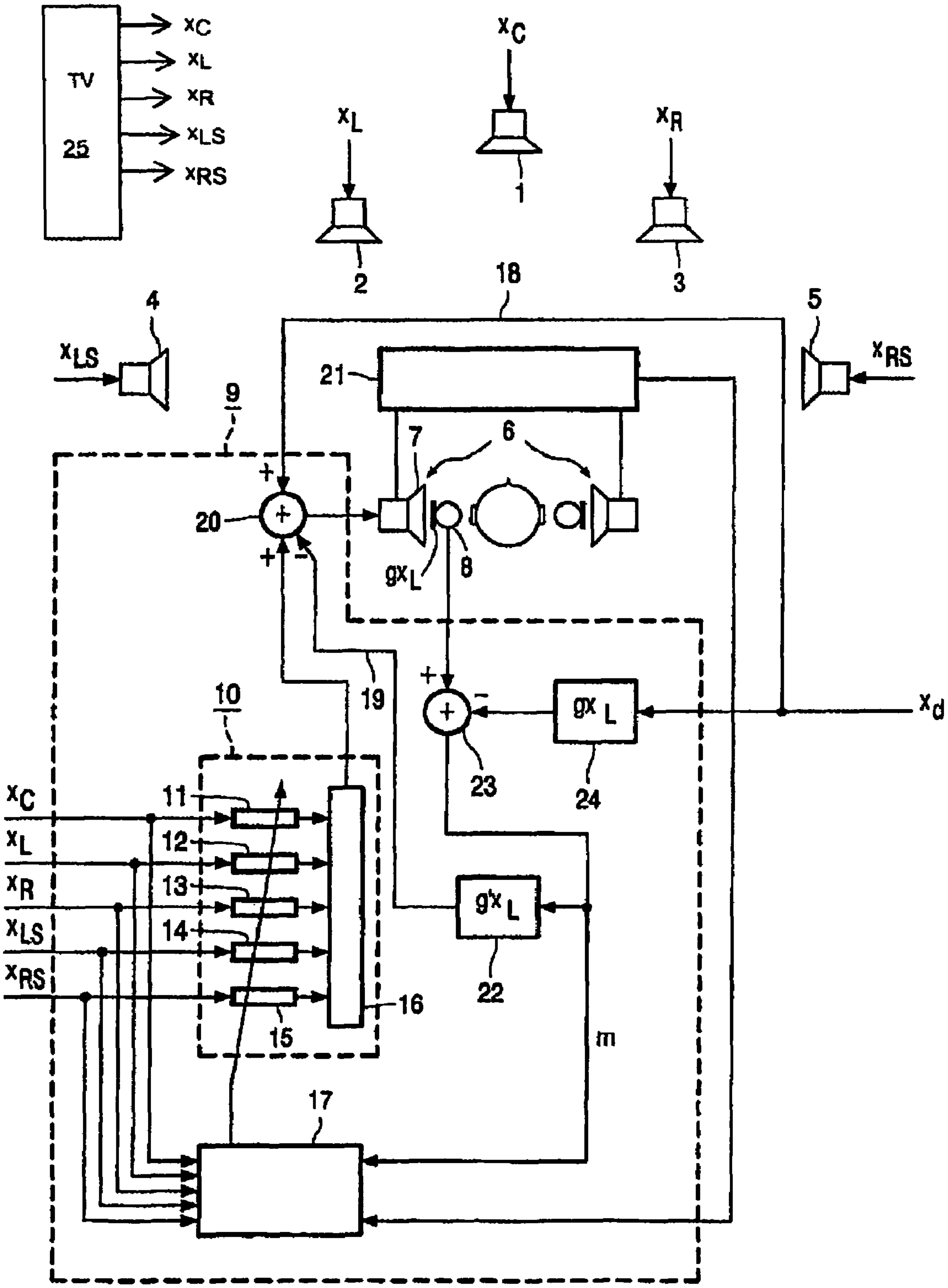
TV
25
$x_C$
$x_L$
$x_R$
$x_{LS}$
$x_{RS}$
1
2
3
4
5
6
7
8
9
10
11
12
13
14
15
16
17
18
19
20
21
22
23
24
$gx_L$
$g'x_L$
$x_d$
m

METHOD FOR CANCELING UNWANTED LOUDSPEAKER SIGNALS

The invention relates to a method for canceling unwanted signals from at least one external sound source, such as a loudspeaker, by means of headphones provided with microphones.

From the international patent application WO 94/30029 a noise cancellation system for headphones is known. In this document a noise cancellation system for canceling unknown low frequency and high frequency, rapidly changing noise is described wherein microphones, included in the headphones, pick up sound signals in the headphones. Based on signals from the microphones the unknown noise is estimated whereafter anti-noise signals are generated by means of a noise cancellation algorithm. These anti-noise signals, supplied to the headphones, reduce the noise. The disadvantage of this method is that all sound signals are suppressed to some extend.

When, for example, someone wants to read a newspaper in quiet, while at the same time someone else is watching television, the application of noise cancellation headphones of the type described above could be the basis for a solution to suppress sound signals from the loudspeakers of the television. However in that case, instead of unknown noise signals, we have known signals which have to be suppressed; an estimation of the noise is not necessary. When, such noise cancellation systems of the above described type are used, the disadvantage mentioned above, i.e. a limited performance, will still be valid. Further, in such systems also other sounds-like conversations in the room, which are not coming from the loudspeakers will be suppressed too.

The purpose of the invention is to find a method for cancellation unwanted signals from at least one external sound source, in which the disadvantages of the above noise cancellation systems are avoided or at least mitigated.

Therefore, according to the invention, there is provided a method for canceling unwanted signals from at least one external sound source, such as a loudspeaker, by means of headphones provided with microphones, wherein at least known sound signals from the at least one external sound source are compensated by sound signals, simulating in antiphase the at least known sound signals from said at least one external sound source, said anti-phase sound signals being generated in the headphones in response to signals derived from input audio signals of the at least one external sound source in a filter device which is controlled by the resulting microphone signals. The advantage of this method is that, because the unwanted signals are already known, no estimation of the noise, i.e. the unwanted signals, is necessary, the cancellation method according to the invention is much easier, while the disadvantages of the cancellation of unknown noise, as indicated above, is avoided.

In a first embodiment, during initialization, the characteristics of the filter device are computed by means of a sound source simulation algorithm, which algorithm controls the characteristics of the filter device such that the signals of the microphones are minimized or become substantially zero.

After this initialization, the filter device is fixed. Although this embodiment is relatively simple to implement, the cancellation of the unwanted sound signals will only work if the headphones listener does not move his or her head.

Therefore in a preferred, second embodiment, to obtain a set of different filter characteristics, the process of computing is performed on various places in the direct neighborhood of the listening position, while during sound reproduction one set of said filter characteristics is selected by means of the algorithm, depending on the position of the head of the person who wears the headphones, which position is indicated by a head tracker. It may be noted that head trackers are known per se, for example from European patent application EP-A-0 762 803.

The method of suppression of known unwanted signals may be combined with a reducing of unknown unwanted, particularly environmental noise signals. In that case the method according to the invention is further characterized in that, while known unwanted signals from the at least one external sound source are suppressed, unknown unwanted, particularly environmental noise signals are reduced by deriving from the microphone signals further signals which, after being converted into sound signals represent in antiphase said unknown unwanted signals.

It is desired that the person wearing the headphones may listen to his or her own music, while the unwanted signals from the at least one external sound source are suppressed. Therefore, further according to the invention, the method is characterized in that, while unwanted signals from the at least one external sound source are suppressed, a further audio input signal is supplied to the headphones and a correction signal is applied to the microphone signal, said correction signal being derived from said further audio input signal such that the corrected microphone signals are still minimized or become still substantially zero.

The invention also relates to a sound reproducing system, for applying the method described above, comprising headphones with sound generating means and with microphones, and control means, the control means being provided with a filter device to control the sound signal generated by said sound generating means to simulate at least one external sound source in response to a known audio input signal and with regulation means to regulate said filter device such that the signals supplied by the microphones and fed to the control means are minimized or substantially zero when said known audio input signal is also supplied to said at least one external sound source. Particularly the control means comprise a sound source simulation algorithm to determine one or more sets of filter characteristics, each set of filter characteristic corresponding with one position of the head of the person who wears the headphones. In case more sets of filter characteristics are established, a head tracker is provided by means of which the position of the head of the person who wears the headphones can be determined. The international patent application WO 01/49066 shows a similar sound reproducing system. However, the control device works different; the system in said international patent application is operable in the following two phases: In a first phase the filter device is adjusted in such a manner that by means of an audio input signal supplied to the filter device a signal is generated in the sound generating means which compensates the audio input signal. Then, in a second phase the at least one external sound source is made inoperative, so that the sound generating means provide for a sound reproduction through the microphones which simulates the at least one external sound source. The first phase is introduced for measuring the transfer functions from external sound sources (loudspeakers) to the microphones in headphones inside a listener ears. The sound is than generated by passing the audio signals through the filter means, adjusted to these transfer functions, and reproducing the resulting sound through the headphones.

As the suppression of known unwanted sound signals may be combined with a reducing of unknown unwanted, particularly environmental noise sound signals, the control means can further comprise combination means and correction means to provide, in response to the microphone signals, for signals, which, supplied to the sound generating means, reduce unknown unwanted, particularly environmental noise signals, the transfer function of the correction means being such that the product of the latter transfer function with the transfer function of the sound generating means to the microphones is about 1 (one) over a certain frequency range.

To make it possible that the person wearing the headphones may listen to his or her own music, while the unwanted signals from the at least one external sound source are suppressed, the control means may further comprise combination means and further correction means to insert a further sound signal to the sound generating means and to correct the microphone signal with a correction signal derived from said further audio input signal, the transfer function of the correction means substantially being the same as the transfer function of the sound generating means to the microphones.

The invention further relates to an algorithm, applied in the method described above, for processing the above filter device.

The invention will be apparent from and elucidated with reference to the example as described in the following and to the accompanying drawing, which shows in FIG. 1 schematically the sound reproducing system according to the invention.

In the example described there are five external sound sources in the form of loudspeakers 1-5, viz. for an audio center channel, left and right channels and surround channels. The audio input signals for these loudspeakers are indicated by respectively $x_C$, $x_L$, $x_R$, $x_{Ls}$ and $x_{Rs}$, in general xi. These audio input signals may be generated by an audio signal source, such as television (TV) 25 In the center of the FIGURE the head of a person is indicated; this person carries headphones 6 with sound generating means 7 and microphones 8. The processing according to the invention is only considered for the left ear of said person as the processing for the right ear is likewise. The microphone 8 supplies a microphone signal m in response to sound signals from the loudspeakers 1-5 and from the sound generating means 7. The input signal of the sound generating means 7 is supplied by control means 9. These control means comprise a filter device 10 with filters 11-15 and combination means 16, and regulating means 17. The transfer function of the filters 11-15 is indicated by respectively $h_{C,L}$, $h_{L,L}$, $h_{R,L}$, $h_{Ls,L}$ and $h_{Rs,L}$, in general $h_{i,L}$. The input signals of these filters are chosen for sake of simplicity to be the same as the input signals for the loudspeakers, viz. $x_C$, $x_L$, $x_R$, $x_{Ls}$and $x_{Rs}$ respectively, originating from, for example, TV 25. The filter device 10 supplies a signal $\Sigma\, x_i \cdot h_{i,L}$ to the sound generating means 7. The "point" in this and following mathematical expressions means a multiplication in the frequency domain and a convolution in the time domain of the relevant signals and functions.

Apart from the signal supplied to the sound generating means 7 via lines 18 and 19 and the combination means 20, which will be discussed later on, the output signal of the sound generating means 7 established by the microphone 8 can be represented by $gx_L.\Sigma\, x_i.h_{i,L}$ with $gx_L$ the transfer function of the sound generating means 7 to the left microphone 8. When the transfer functions from the loudspeakers 1-5 to the left microphone 8 are represented by $gx_{C,L}$, $gx_{L,L}$, $gx_{R,L}$, $gx_{Ls,L}$ and $gx_{Rs,L}$, in general $gx_{i,L}$, than the signal m from the left microphone 8 can be represented by:

$$m=\Sigma x_i.[h_{i,L}.gx_L+gx_{i,L}].$$

The filters characteristics are computed and regulated by means of a sound source simulation algorithm in the regulation means such that m is minimized, with m=0 in the ideal situation. This means that, after initialization, the signals from the sound generating means 7 are equal to the signals from the loudspeakers, but in anti-phase, and thus that by means of said filters the sound signals from the loudspeakers are simulated.

When the filters 11-15 are adjusted, during initialization, in such a way that the microphone signal m is minimized the desired cancellation of the loudspeaker signals will be obtained. In that case the transfer functions of the filters 11-15: $h_{i,L}=-gx_{i,L}/gx_L$, are fixed.

When the person wearing the headphones moves or takes another location, the transfer functions from the loudspeakers 1-5 to the microphones change, so that the transfer functions of the filters 11-15 do not correspond any longer with forms with m minimized. Although in that case the initialization can be repeated for the new position, it may be an advantage when in the initialization phase for a number of head positions and/or neighboring positions a set of filter characteristics is established and stored in the regulation means 17. By means of a known head tracker 21, preferably mounted on the headphones 6 the position of the head of the person wearing the headphones can be established and a specific set of filter characteristics can be selected therewith. In some cases, for example, when the tracking rate of the head tracker is not sufficient, it is of advantage that a filter with fixed filter characteristics is used or with filter characteristics which, each time the head of the person wearing the headphones moves, are gauged (updated) continuously.

When the suppression of known unwanted sound signals will be combined with a reducing of unknown unwanted sound signals, such as environmental noise signals, the microphone signal may be supplied to correction means 22, while the output signal of said correction means 22 is supplied to the sound generating means 7 via the line 19 and the combination means 20, wherein said output signals are combined with the signals from the filter device 10. The transfer function of the correction means 22, viz. $g'x_L$, is such that the product of the latter transfer function with the transfer function of the sound generating means 7 to the microphones 8 is about 1 (one) over a certain frequency range:

$$gx_L.g'x_L\approx 1.$$

The sound generating means 7 reproduce sound signals which approach the unknown unwanted sound signals, but in anti-phase, which leads to a reduction of said unknown unwanted sound signals.

When the person wearing the headphones likes to listen to some music, a desired audio signal $x_d$ thereof may be supplied to the combination means 20 via the line 18 and added to the signals from the filter device 10. However, in that case in the expression for m, a term $x_d.gx_L$ is introduced. In order to compensate for this term in the connection between the microphone 8 and the regulation device 17 combination means 23 are inserted. In these combination means 23 the value of the microphone signal is diminished with a value $x_d.gx_L$, derived from further correction means 24. The transfer function of these further correction means 24 is substantially the same as the transfer function from the sound generating means 7 to the microphone 8.

By means of the above described sound reproducing system, after initialization, known unwanted signals from the loudspeakers are suppressed, independent of the position where the person, carrying the headphones, is located in the room where the loudspeakers are arranged, while further optionally unknown unwanted sound signals can be reduced.

The method and the embodiment described above may be realized by an algorithm, at least part of which may be in the form of a computer program capable of running on signal processing means in an audio apparatus or cooperating with an audio apparatus comprising the sound reproducing system according to the invention. In so far part of the FIGURE shows units to perform certain programmable functions, these units can be considered as subparts of the computer program.

It may be noted that, although not indicated in the FIGURE, corresponding control means are provided to suppress unwanted signals in the right ear.

The invention is not restricted to the described embodiment. Modifications are possible. For example, the number of external sound sources is irrelevant. The audio input signals applied to the filters need not to be equal to the audio input signals of the loudspeakers; it is sufficient when there is a relation between both audio input signals.

The invention claimed is:

1. A method for canceling unwanted sound signals from at least one external sound source, said unwanted sound signals resulting from electrical audio signals applied to the at least one external sound source, when using headphones provided with microphones, wherein at least the unwanted sound signals from the at least one external sound source are compensated by generated sound signals, said method comprising the steps:

receiving, as audio input signals, said electrical audio signals as applied to said at least one external sound source;

filtering said received audio input signals, under control of resulting signals from said microphone, thereby deriving compensating signals; and generating anti-phase sound signals in the headphones in response to said compensating signals.

2. The method for canceling unwanted sound signals from at least one external sound source as claimed in claim 1, wherein, during an initialization phase, said method comprises the step of:

computing the characteristics of the filter device using a sound source simulation algorithm, said algorithm controlling the characteristics such that the signals of the microphones are minimized or become substantially zero.

3. The method for canceling unwanted signals from at least one external sound source as claimed in claim 2, wherein in said initialization phase, said method comprises performing said computing step in various places in the direct neighborhood of a listening position in order to obtain a set of different filter characteristics, and wherein, during sound reproduction, said method comprises the step of:

choosing one set of said filter characteristics using the algorithm, in dependence on the position of the head of the person using the headphones, said position being indicated by a head tracker.

4. The method for canceling unwanted signals as claimed in claim 1, characterized in that said method further comprises the steps of:

deriving, from the microphone, further signals, corresponding to unknown unwanted, particularly environmental noise signals; and generating further anti-phase sound signals in said headphones in response to said further signals, for reducing said unknown unwanted signals.

5. The method for canceling unwanted signals from at least one external sound source as claimed in claim 1, characterized in that said method further comprises the steps of:

supplying a further audio input signal to the headphones;

generating a correction signal from said further audio input signal; and applying said correction signal to the microphone signal, whereby corrected microphone signals are minimized or become substantially zero.

6. A computer-readable medium carrying instructions to be executed by signal processing means, the instructions enabling said signal processing means to perform the method as claimed in claim 1.

7. A sound reproducing system comprising headphones having sound generating means and microphones, and control means for canceling unwanted sound signals from at least one external sound source when using said headphones, said unwanted sound signals resulting from electrical audio signals applied to the at least one external sound source, wherein the control means comprises:

an input for receiving, as audio input signals, said electrical audio signals as applied to said at least one external sound source;

a filter device for filtering said received audio input signals, said filter device deriving compensating signals; and regulation means, coupled to receive signals from the microphones, for regulating said filter device such that the compensating signals, applied to the headphones in anti-phase, cancel sound signals generated by said at least one external sound source, and the signals supplied by the microphones are minimized or substantially zero.

8. The sound reproducing system as claimed in claim 7, characterized in that the control means comprises a sound source simulation algorithm for determining one or more sets of filter characteristics, each set of filter characteristics corresponding with one position of the head of the person wearing the headphones.

9. The sound reproducing system as claimed in claim 7, characterized in that said sound reproducing system further comprises a head tracker for determining the position of the head of the person wearing the headphones.

10. The sound reproducing system as claimed in claim 7, characterized in that the control means further comprises:

correction means, coupled to receive the microphone signals, for generating correction signals; and combination means for combining said correction signals from said correction means and said compensating signals from said filter device, whereby said correction signals, when supplied to the sound generating means, reduce unknown unwanted, particularly environmental noise signals, and wherein a product of a transfer function of the correction means a transfer function of the sound generating means to the microphones is about 1 (one) over a certain frequency range.

11. The sound reproducing system as claimed in claim 10, characterized in that the control means further comprises:

a further input for receiving a further audio input signal;

further correction means coupled to said further input for forming a further correction signal; and further combination means for combining said corrected input signal with said microphone signals, an output of said further combination means being coupled to said regulation means, wherein the microphone signals are corrected by the further correction signal derived from said further audio input signal, and wherein a transfer function of the further correction means is substantially the same as the transfer function of the sound generating means to the microphones.

12. An audio apparatus, provided with the sound reproducing system as claimed in claim 7.

* * * * *